(12) United States Patent
Kachelriess et al.

(10) Patent No.: US 8,891,885 B2
(45) Date of Patent: Nov. 18, 2014

(54) METHOD, COMPUTING UNIT, CT SYSTEM AND C-ARM SYSTEM FOR REDUCING METAL ARTIFACTS IN CT IMAGE DATASETS

(75) Inventors: Marc Kachelriess, Nürnberg (DE); Esther Meyer, Erlangen (DE); Rainer Raupach, Heroldsbach (DE)

(73) Assignee: Siemens Aktiengesellschaft, Munich (DE)

( * ) Notice: Subject to any disclaimer, the term of this patent is extended or adjusted under 35 U.S.C. 154(b) by 182 days.

(21) Appl. No.: 13/562,478

(22) Filed: Jul. 31, 2012

(65) Prior Publication Data
US 2013/0039556 A1 Feb. 14, 2013

(30) Foreign Application Priority Data

Aug. 10, 2011 (DE) .......................... 10 2011 080 727
Apr. 24, 2012 (DE) .......................... 10 2012 206 714

(51) Int. Cl.
*G06K 9/00* (2006.01)
*A61B 6/03* (2006.01)
*G06T 5/50* (2006.01)
*A61B 6/00* (2006.01)
*G06T 11/00* (2006.01)
*G06T 5/00* (2006.01)

(52) U.S. Cl.
CPC ... *A61B 6/00* (2013.01); *A61B 6/03* (2013.01); *G06T 2207/10081* (2013.01); *G06T 5/50* (2013.01); *G06T 11/008* (2013.01); *G06T 5/003* (2013.01); *A61B 6/5282* (2013.01)
USPC ..................................... 382/232

(58) Field of Classification Search
None
See application file for complete search history.

(56) References Cited

U.S. PATENT DOCUMENTS

| 2006/0285737 | A1* | 12/2006 | Hamill et al. ................. 382/131 |
| 2008/0152203 | A1* | 6/2008 | Bal et al. ...................... 382/131 |
| 2009/0279768 | A1* | 11/2009 | Nishikawa .................... 382/132 |
| 2011/0007956 | A1 | 1/2011 | Meyer et al. |
| 2011/0081071 | A1* | 4/2011 | Benson et al. ................ 382/154 |

FOREIGN PATENT DOCUMENTS

DE 102009032059 A1 1/2011

OTHER PUBLICATIONS

Reduction of CT artifacts caused by metallic implants Kalender et al.; Radiology vol. 164, No. 2, Seiten 576-577; Radiology; Magazine; 1987.
A.H. Mahnken et al.; A new algorithm for metal artifact reduction in computed tomography: in vitro and in vivo evaluation after total hip replacement Invest Radiol. Dec. 2003;38(12):769-775; Others; 2003.

(Continued)

Primary Examiner — Hadi Akhavannik
(74) Attorney, Agent, or Firm — Harness, Dickey & Pierce, P.L.C.

(57) ABSTRACT

A method is disclosed for reducing metal artifacts in CT image datasets. An embodiment of the method includes reconstructing a first CT image dataset with and a second CT image dataset without metal artifact correction, weighted summation of a high-pass-filtered first and a high-pass-filtered second CT image dataset plus a low-pass-filtered second CT image dataset, wherein the weightings are dependent on the proximity to metal in the CT image datasets. A computing unit, a CT system and a C-arm system designed to execute the method are also disclosed.

18 Claims, 6 Drawing Sheets

(56) References Cited

OTHER PUBLICATIONS

Marc Kachelrieβ et al.;Institute of Medical Physics, University of Erlangen-Nürnberg, Germany; "Generalized multi-dimensional adaptive filtering for conventional and spiral single-slice, multi-slice, and cone-beam CT"; Med.Phys. 28 (4), Apr. 2001; pp. 475-490.; Book; 2001.

Bruno DeMan et al; An Iterative Maximum-Likelihood Polychromatic Algorithm for CT; IEEE Transactions on Medical Imaging, vol. 20, No. 10, Oct. 2001.; Others; 2001.

Esther Meyer et al., "Normalized metal artifact reduction (NMAR) in computed tomography", Med.Phys. 37 (10), Oct. 2010, S. 5482-5493; Others; 2010.

Yiannis Kyriakou et al., "Empirical beam hardening correction (EBHC) for CT", Med.Phys. 37 (10), Oct. 2010, S.5179-5187; Others; 2010.

Catherine Lemmens et al., "Suppression of Metal Artifacts in CT Using a Reconstruction Procedure That Combines MAP and Projection Completion", IEEE Transactions on Medical Imaging, vol. 28. No. 2, Feb. 2009; Others; 2009.

Hiroyuki Kudo et al., "New Approximate Filtered Backprojection Algorithm for Helical Cone-Beam CT with Redundant Data", 0-7803-8257-9/04, 2004 IEEE; Others; 2004.

Gilad Shechter et al., "High-Resolution Images of Cone Beam Collimated CT Scans", IEEE Transactions on Nuclear Science, vol. 52, No. 1, Feb. 2005, S. 247-255; Others; 2005.

Priority Document German Application No. 102011080727.6 filed Aug. 8, 2011.

Priority Document German Application No. 102012206714.0 filed Apr. 24, 2012.

Key Young Jeong et al; "Metal Artifact Reduction Based on Sinogram Correction in CT"; 2009 IEEE Nuclear Science Symposium Conference Record, (NSS/MIC2009) Orlando, Florida; pp. 3480-3483; 2009; US.

German Office Action mailed Aug. 27, 2014.

* cited by examiner

METHOD, COMPUTING UNIT, CT SYSTEM AND C-ARM SYSTEM FOR REDUCING METAL ARTIFACTS IN CT IMAGE DATASETS

PRIORITY STATEMENT

The present application hereby claims priority under 35 U.S.C. §119 to German patent application numbers DE 10 2011 080 727.6 filed Aug. 10, 2011 and DE 10 2012 206 714.0 filed Apr. 24, 2012, the entire contents of each of which are hereby incorporated herein by reference.

FIELD

At least one embodiment of the invention generally relates to a method, a computing unit, a CT system and/or a C-arm system for reducing metal artifacts in CT image datasets.

BACKGROUND

Methods for reconstructing tomographic image datasets from detector data from a scan of an object by a CT system are generally known. If metal items are located in the object, strong image artifacts, known as metal artifacts, which appreciably reduce the quality of the reconstructed image, arise on account of increased beam hardening, more scattered radiation, a partial volume effect and increased noise.

To reduce such metal artifacts a wide variety of methods is known. These can be divided into three groups:

Interpolation-based methods, as described for example in the publications W. A. Kalender, R. Hebel, and J. Ebersberger, "Reduction of CT artifacts caused by metallic implants," Radiology, vol. 164, no. 2, pp. 576-577, August 1987, and A. H. Mahnken, R. Raupach, J. E. Wildberger, B. Jung, N. Heussen, T. G. Flohr, R. W. Gunther, and S. Schaller, "A new algorithm for metal artifact reduction in computed tomography: in vitro and in vivo evaluation after total hip replacement," Investigative Radiology, vol. 38, no. 12, pp. 769-775, December 2003. The group of interpolation methods also includes an improved method for normalized sinogram interpolation, which is disclosed in the applicant's patent application DE 10 2009 032 059 A1.

Empirical methods, in which individual physical effects are corrected, as described for example in the publications M. Kachelrieβ, O. Watzke, and W. A. Kalender, "Generalized multi-dimensional adaptive filtering (MAF) for conventional and spiral single-slice, multi-slice and cone-beam CT," Med. Phys., vol. 28, no. 4, pp. 475-490, April 2001, and Y. Kyriakou, E. Meyer, D. Prell, and M. Kachelrieβ, "Empirical beam hardening correction (EBHC) for CT", Med. Phys., 37(10):5179-5187, October 2010.

Iterative correction methods, which are described for example in the publications B. De Man, J. Nuyts, P. Dupont, G. Marchal, and P. Suetens, "An iterative maximum-likelihood polychromatic algorithm for CT," IEEE Transactions on Medical Imaging, vol. 20, no. 10, pp. 999-1008, October 2001. and C. Lemmens, D. Faul, and J. Nuyts, "Suppression of Metal Artifacts in CT Using a Reconstruction Procedure That Combines MAP and Projection Completion", TMI, vol. 28, no. 2, pp. 250-260, February 2009.

Although the above-mentioned methods sometimes produce very good results, residual artifacts always remain, and need to be eliminated.

SUMMARY

At least one embodiment of the invention is directed to finding a more extensive metal artifact reduction method which improves the current methods still further.

Advantageous developments of the invention form the subject matter of subordinate claims.

The inventors have recognized the following:

The proportion of metal artifacts which originates from beam hardening and scattered radiation tends to be located in low-frequency position space. The high frequencies of an image which was reconstructed without metal artifact correction contain, besides edges of anatomical structures, almost nothing but noise. Using a frequency split an image can be generated which has hardly any artifacts, apart from noise, in both high and low frequencies. Hence it is now possible to improve the known methods for reducing metal artifacts by using a suitable frequency split method, in that a results image dataset is compiled from the weighted high-frequency parts of a non-metal-artifact-corrected CT image dataset and from the weighted high-frequency parts of a CT image dataset which is metal-artifact-corrected in accordance with known methods, wherein in the vicinity of metal artifacts the high-frequency parts of the metal-artifact-corrected CT image dataset are increasingly weighted, while in image regions further from the metal the high-frequency parts of the non-metal-artifact-corrected CT image dataset are increasingly weighted; additionally the low-frequency parts of the metal-artifact-corrected CT image dataset are added unweighted, in order to obtain a CT image dataset containing all spatial frequencies.

Accordingly, in at least one embodiment the inventors propose a method for reducing metal artifacts in CT image datasets, in which reconstruction is used to generate a first CT image dataset with and a second CT image dataset without metal artifact correction and a weighted summation of a high-pass-filtered first and a high-pass-filtered second CT image dataset plus a low-pass-filtered second CT image dataset is effected, the weightings being dependent on the proximity to metal in the CT image datasets.

BRIEF DESCRIPTION OF THE DRAWINGS

The invention is described in greater detail below on the basis of the preferred exemplary embodiments with the aid of the figures, wherein only the features necessary to understand the invention are shown. The following reference characters are used: AF: adaptive filtering; C1: CT system; C2: first emitter; C3: first detector; C4: second emitter; C5: second detector; C6: gantry housing; C8: patient couch; C9: system axis; C10: control and processing system; FSMAR: results image; G: weighting mask for metal; HP: high-pass filter; HPF: high-pass filtering; MAR_high: high-pass-filtered metal-artifact-corrected CT image dataset; MAR_low: low-pass-filtered metal-artifact-corrected CT image dataset; MET: generation of a weighting mask G for metal that is present; P: patient; Prg1-Prgn: computer programs; RECON: reconstruction; RECON+MET_CORR: reconstruction with metal correction; RD: raw detector data; SCAN: CT scan; TP: low-pass filter; TPF: low-pass filtering; U: uncorrected first CT image dataset; U_af: adaptively filtered CT image dataset; U_high: high-pass-filtered first image dataset.

The individual figures show.

DETAILED DESCRIPTION OF THE EXAMPLE EMBODIMENTS

Figure 1:
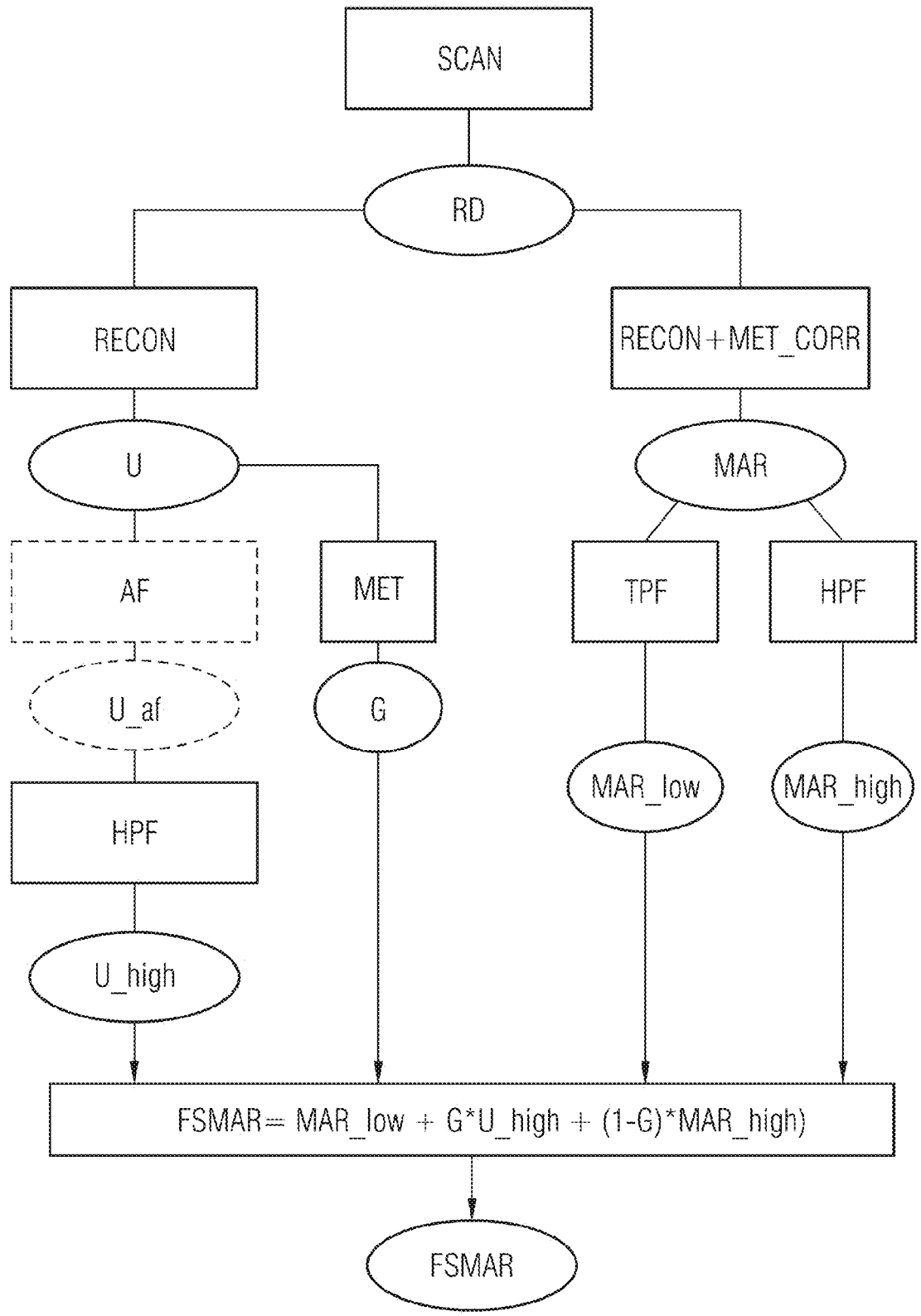
FIG. 1: Method sequence of a variant of an embodiment of an inventive metal artifact correction.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Accordingly, in at least one embodiment the inventors propose a method for reducing metal artifacts in CT image datasets, in which reconstruction is used to generate a first CT image dataset with and a second CT image dataset without metal artifact correction and a weighted summation of a high-pass-filtered first and a high-pass-filtered second CT image dataset plus a low-pass-filtered second CT image dataset is effected, the weightings being dependent on the proximity to metal in the CT image datasets.

In a concrete variant of the embodiment the method can have the following method steps for reducing metal artifacts in CT image data:
  use of detector data from a scan of an object with incorporated metal,
  reconstruction of a first CT image dataset which dispenses with metal artifact correction,
  filtering of the first CT image dataset with a high-pass filter for generating a high-pass-filtered first CT image dataset,
  extraction of a CT image dataset representing exclusively metal from a first CT image dataset and generation of a metal-weighting function or metal-weighting mask such that image regions containing metal are heavily weighted and image regions without metal are slightly weighted, in particular image regions containing metal are weighted more heavily than image regions without metal, in particular image regions containing metal are weighted with a weighting factor $\geq 0.5$ and image regions without metal are weighted with a weighting factor $<0.5$.
  reconstruction of a second CT image dataset using metal artifact correction,
  filtering of the second CT image dataset with the high-pass filter for generating a high-pass-filtered second CT image dataset,
  filtering of the second CT image dataset with a low-pass filter complementary to the high-pass filter for generating a low-pass-filtered second CT image dataset,
  summation of a results image from the low-pass-filtered second CT image dataset, the metal-weighted high-pass-filtered first CT image dataset and the complementarily metal-weighted high-pass-filtered second CT image dataset, and
  storage and/or output of the results image.

The results image is thus calculated according to the formula FSMAR=MAR_low+G*U_high+(1−G)*MAR_high, where the abbreviation FSMAR for the results image stands for "Frequency Split Metal Artifact Reduction", MAR_low represents the low-pass-filtered metal-artifact-corrected CT image dataset, MAR_high the high-pass-filtered metal-artifact-corrected CT image dataset, U_high the high-pass-filtered uncorrected CT image dataset and G the weighting mask or weighting function.

It is noted that the scope of at least one embodiment of the invention in particular also covers methods which represent combinations of the method steps.

At least one embodiment of the inventive method can be further improved in that in addition the detector data is filtered adaptively with a noise filter before the reconstruction of at least one of the CT image datasets in respect of a noise or a signal-to-noise ratio that is present, a high noise or a low signal-to-noise ratio requiring strong filtering and vice versa.

Likewise it is possible to adaptively filter the first CT image dataset with a noise filter before the high-pass filtering in respect of a noise or a signal-to-noise ratio that is present, a high noise or low signal-to-noise ratio requiring strong filtering and vice versa.

In principle both all known reconstruction methods and all known methods for metal artifact reduction can be used for the method described here. However, it is particularly advantageous if in the second CT image dataset the metal artifact correction is generated by a normalized sinogram interpolation. An example of a method for this is described in the publication E. Meyer, R. Raupach, M. Lell, B. Schmidt, and M. Kachelrieβ, "Normalized metal artifact reduction (NMAR) in computed tomography", Med. Phys., vol. 37, no. 10, pp. 5482-5493, October 2010, and in patent application DE 10 2009 032 059 A1, the entire contents of each of which are hereby incorporated herein by reference, already mentioned in the introduction which deals with the same topic.

It is further favorable if the metal-weighting function or the metal-weighting mask is determined such that in image regions containing metal or their immediate vicinity a weighting of 1 is present and the weighting diminishes continuously to 0 as the distance from the metal increases. Such a weighting mask can easily be generated for example by generating a metal image from one of the reconstructed and if necessary metal-artifact-corrected CT image datasets, for example by simply forming a threshold via the preferably non-metal-artifact-corrected CT image dataset, and applying a low-pass filter to this metal image which exclusively shows metal.

Besides embodiments of the inventive method, in at least one embodiment the inventors also propose a computing unit with a program memory for storing program code and a processor for executing the program codes, wherein program code which executes an embodiment of the inventive method steps during operation is to be stored in the memory.

Such a computing unit can work equally on a standalone basis, in a network or when directly connected to a CT system or a C-arm system.

FIG. 1 shows a method diagram of an embodiment of an inventive metal artifact correction. In the method step SCAN a tomographic scan of a patient is first performed, to obtain detector data or raw detector data RD. Based on this detector data any known reconstruction without metal artifact correction is then performed on the one hand in the method step RECON, from which the—in respect of metal artifacts—uncorrected CT image dataset U is produced. This uncorrected CT image dataset U can now optionally in the method step AF undergo filtering with a noise-dependent adaptive filter, the result of which is an adaptively filtered CT image dataset U_af. In the method step HPF the high-pass part U_high is calculated from the respective CT image dataset U or U_af by using a high-pass filter.

Furthermore, in the method step MET a weighting mask G, which describes the proximity of the pixels in the image to the metal present there, is generated with the aid of the uncorrected CT image dataset U. The resulting weightings correspond to a value 1 in or directly on the metal and approach the value 0 as the distance increases.

In parallel to this method branch a reconstruction of a CT image dataset is performed in the method step RECON+ MET_CORR from the detector data RD using known additional metal artifact correction, so that a metal-artifact-corrected CT image dataset MAR is produced. Preferably a method can be used here with the aforementioned normalized sinogram interpolation NMAR. The resulting corrected CT image dataset MAR then undergoes low-pass and high-pass filtering in the method steps TPF and HPF, from which the CT image datasets MAR_low and MAR_high are produced. It should be noted here that on the one hand both high-pass filters HP used in this method should be identical and the low-pass filter TP should be complementary to the high-pass filter, so that TP=1−HP.

In the last method step the results image FSMAR is calculated from these results described above according to the formula $$FSMAR = MAR\_low + G * U\_high + (1-G) * MAR\_high.$$

The results image FSMAR can then be output or saved for further use.

Figure 2:
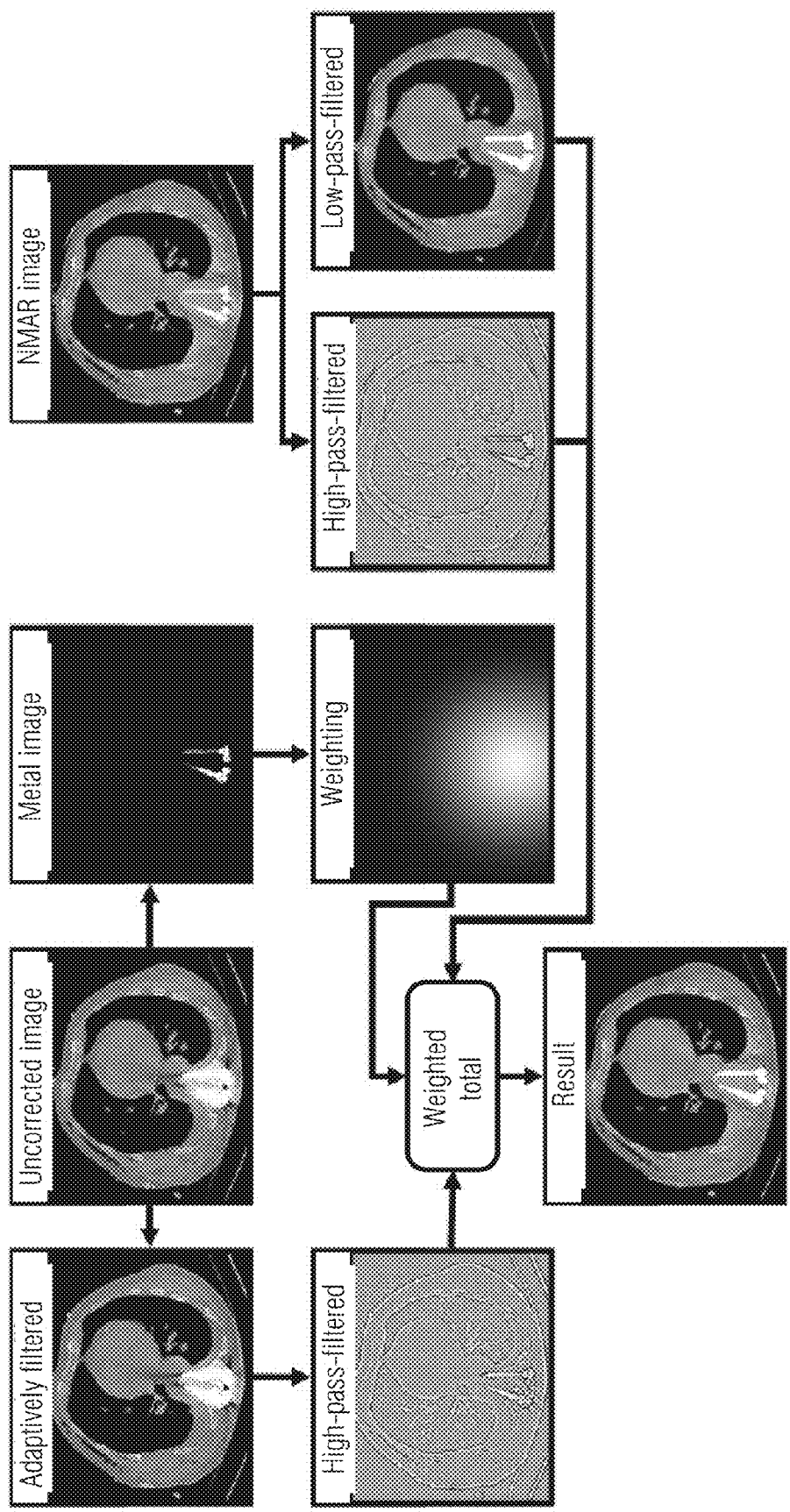
FIG. 2: Alternative representation of the method sequence according to FIG. 1.

FIG. 2 shows an alternative representation of an embodiment of the frequency split method for metal artifact correction described for FIG. 1, wherein the respective associated representations are shown here in the individual method symbols. Accordingly this gives the following method sections:

1—Preprocessing
1A—Adaptive filtering

Firstly an adaptive filter is applied to the raw data. In standard methods with data replacement this is not necessary, as in particular the data in the metal shadow is the noisiest data, and is fully replaced there. However, since in an embodiment of the inventive correction data from the metal shadow is used, noise reduction is recommended.

1B—Segmenting of the Metal Image

An uncorrected image is then reconstructed, from which a metal image is segmented for each threshold operation. This metal image is used both for the first metal artifact correction algorithm (step 2) and also for localized weighting in the frequency split (step 3B).

2—Metal Artifact Correction I (Data Replacement)

Calculation of a metal-artifact-reduced image using an approach in which measured data is replaced or used with a lower weighting. The actual correction of the raw data takes place in this step, wherein however necessarily a loss of information occurs. As described in many publications, the data in the metal track can be replaced by different variants of interpolation/inpainting. In particular the NMAR method is recommended for this, but another method can also be selected.

3—Metal Artifact Correction II (Frequency Split)
3A—Frequency Split

The metal-artifact-reduced image MAR calculated in step 2 is low-pass filtered MAR_low, for example with a Gaussian filter. The corresponding high frequencies MAR_high are calculated by subtracting MAR-image and low-pass-filtered MAR-image. The adaptively filtered, uncorrected image U is correspondingly high-pass filtered U_high.

3B—Weighted Total

The high-frequency part of the uncorrected image contains both important edge information near the metal implant as well as increased noise.

In order not to unnecessarily increase the noise in regions far away from metal implants, a weighting is calculated for each pixel. For this the metal image is binarized, smoothed with a strong low-pass and used as a spatially varying weighting mask G.

The high frequencies of the uncorrected image are multiplied by the metal-weighting mask G, and correspondingly the high frequencies of the MAR image by the weighting 1−G. The corrected image FSMAR is thus as follows:

$$FSMAR = MAR\_low + G * U\_high + (1-G) * MAR\_high.$$

The additional step entails only an extremely small additional calculation requirement with it, as an uncorrected image is always calculated as a first step and linear filters can be efficiently implemented.

Figure 3:
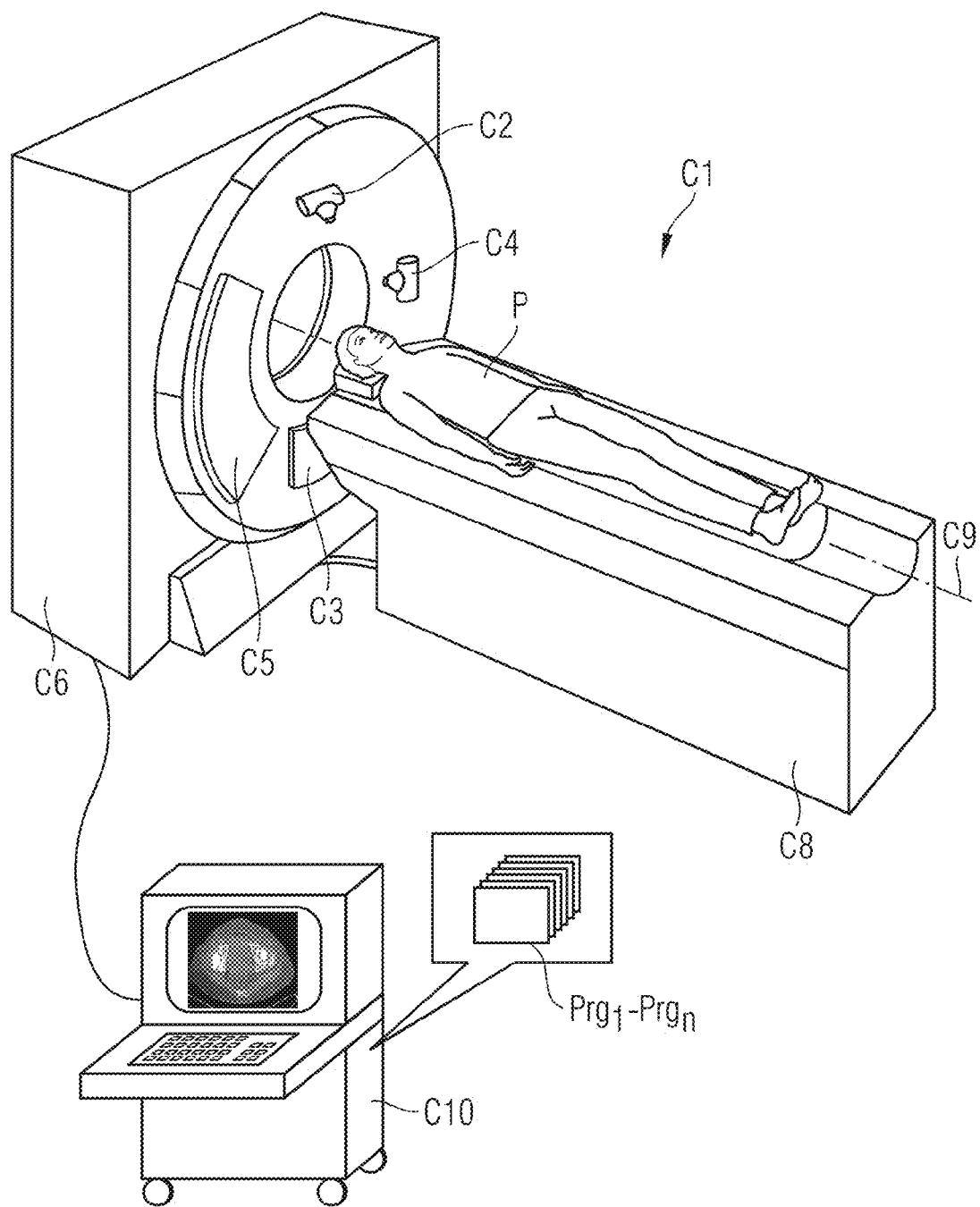
FIG. 3: CT system for implementing an embodiment of an inventive metal artifact correction.

A CT system can be used for the execution of an embodiment of the inventive method for example, as illustrated in FIG. 3. The CT system C1 shown consists of the gantry housing C6 with an emitter C2 arranged on the gantry and an opposing detector C3. Optionally another emitter-detector system, including a second emitter C4 and a second detector C5, can be used, in order for example to achieve a higher temporal or energy resolution. During the CT examination the patient couch C8, arranged so as to move along the system axis C9, guides the patient P continuously or sequentially through the measurement field scanned by the emitter-detector systems and thereby takes projections of the patient P in a plurality of projection directions, which are passed to the control and processing system C10 in the form of detector data. The control of the system is effected by the control and processing system C10, in which computer programs Prg1-Prgn are also stored, which execute an embodiment of the inventive method during operation and thereby generate CT image datasets in 2D or 3D, which even in the presence of metal elements in the region of the scan result in better final results compared to the prior art.

Often metal implants are directly the reason why a CT scan is necessary. Thus the success of an operation can be verified, the reason for problems with a prosthesis examined or a further operation scheduled. In these cases the representation of the area directly surrounding the implant is essential. For automatic evaluations a good method for reducing metal artifacts is likewise important. But even if other regions of the image are of greater interest, an improved image quality throughout the volume is desirable.

Figure 4:
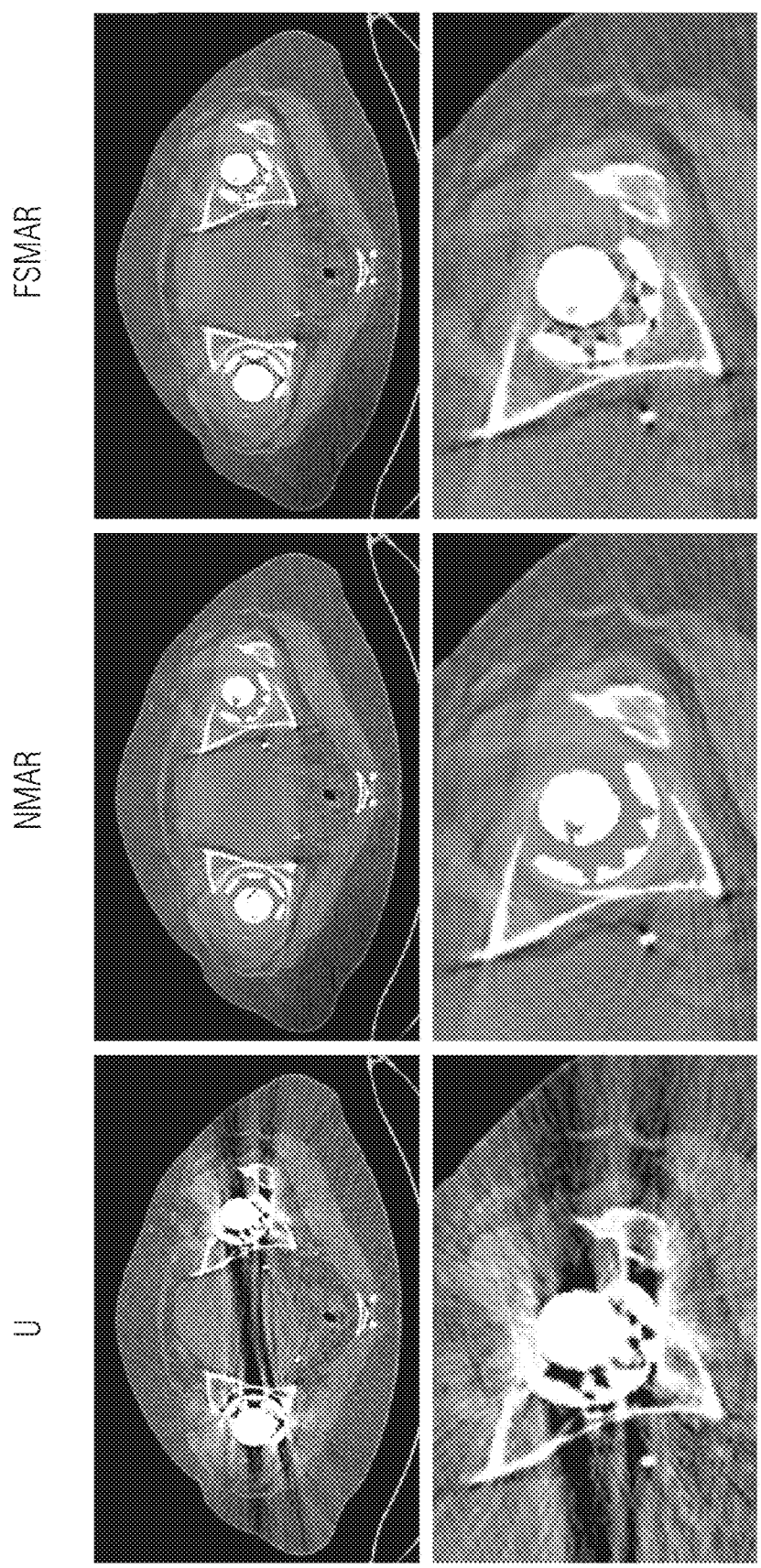
FIG. 4: CT representation of a patient in the pelvic region with bilateral hip prosthesis without metal artifact correction (left), with metal artifact correction after normalized sinogram interpolation (center) and an embodiment of an inventive metal artifact correction (right), in each case in a general recording (top) and a detailed representation (bottom)
Figure 5:
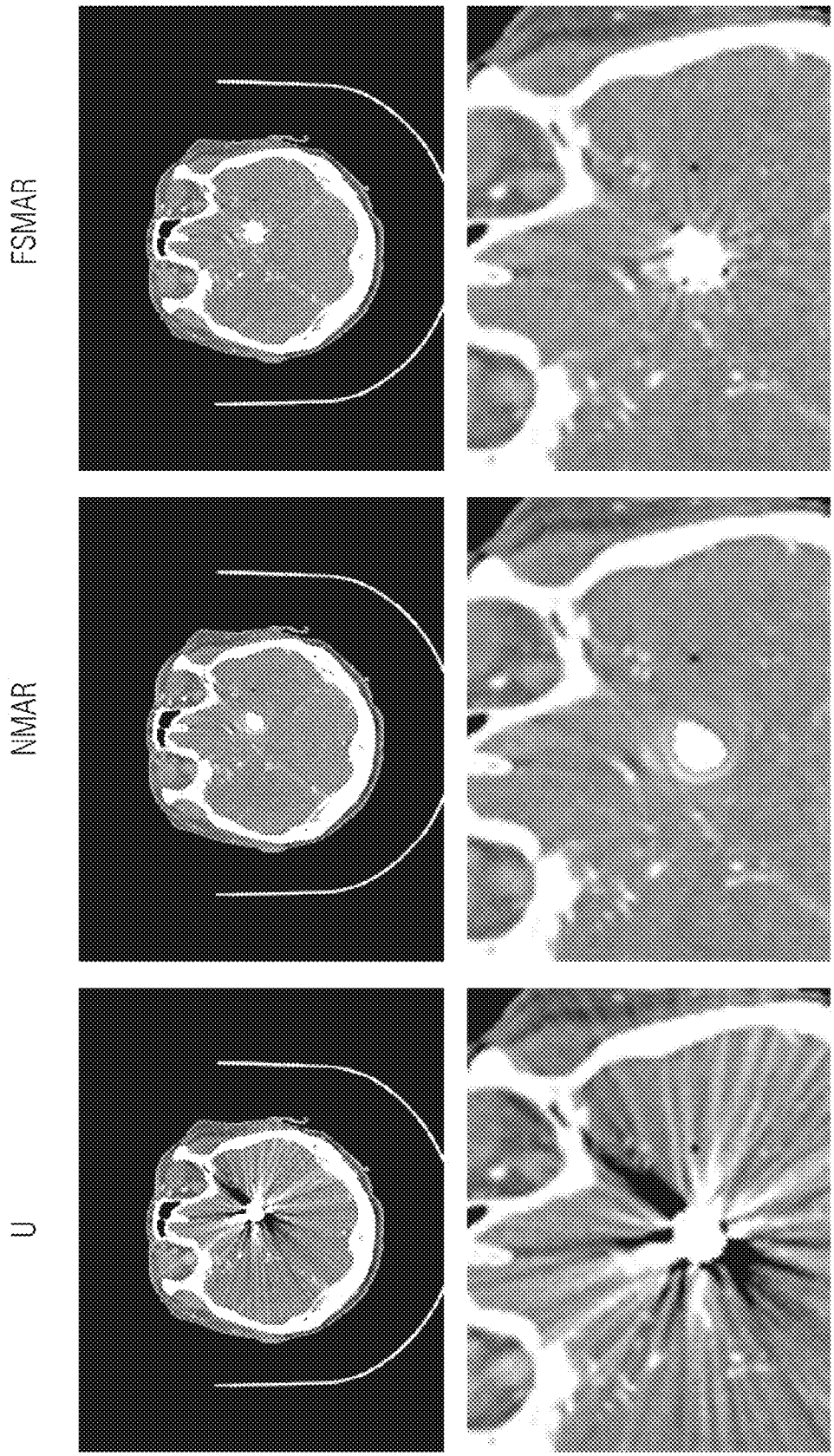
FIG. 5: CT representation of a patient in the head region with an aneurism and inserted neurocoil without metal artifact correction (left), with metal artifact correction after normalized sinogram interpolation (center) and an embodiment of an inventive metal artifact correction (right), in each case in a general recording (top) and a detailed representation (bottom)
Figure 6:
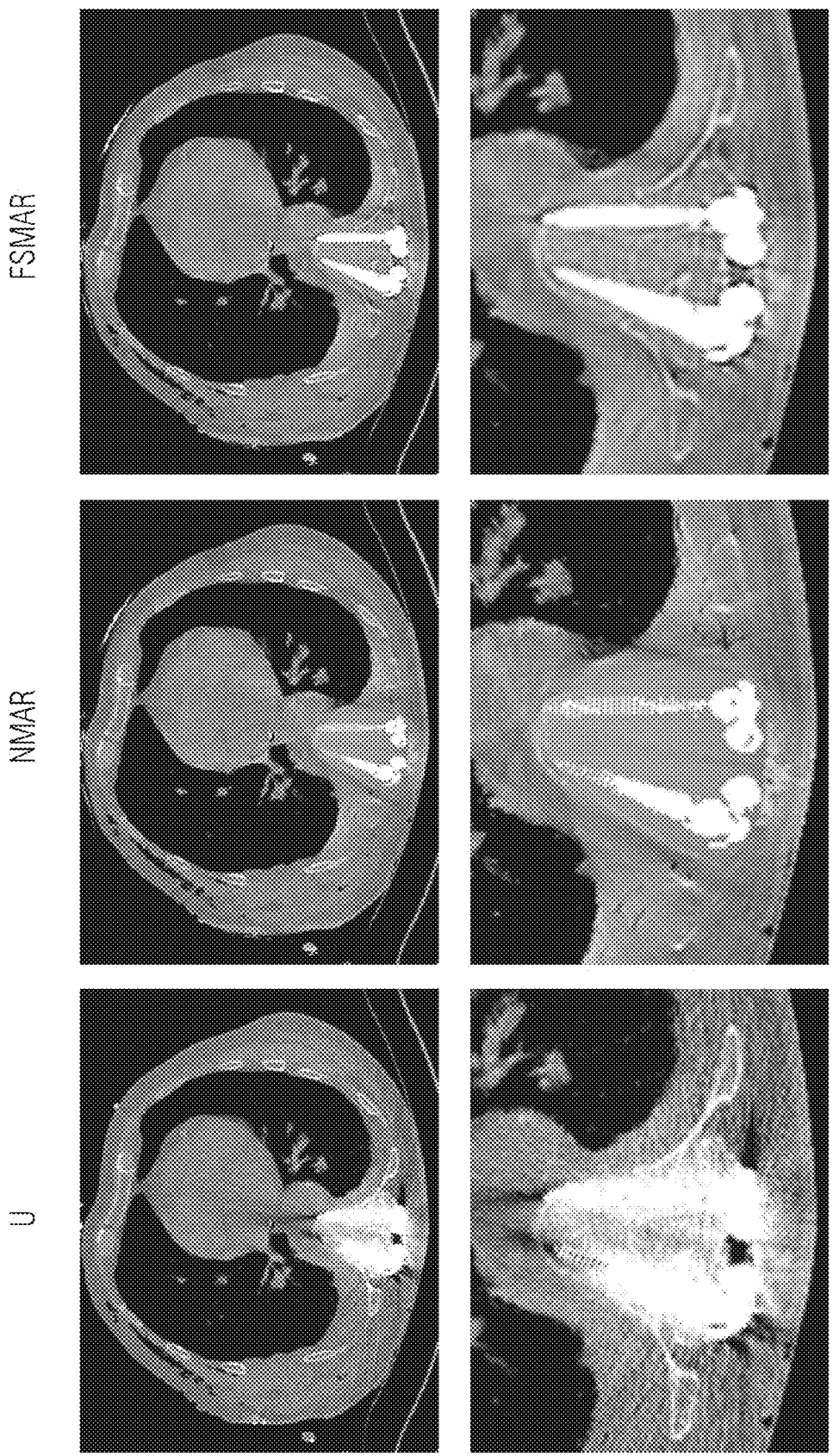
FIG. 6: CT representation of a patient in the breast region with a metal fixing of the spinal column without metal artifact correction (left), with metal artifact correction after normalized sinogram interpolation (center) and an embodiment of an inventive metal artifact correction (right), in each case in a general recording (top) and a detailed representation (bottom).

FIGS. 4 to 6 show three explicit examples of such an improvement. For comparison, in each case a CT representation of a patient with a metal implant without metal artifact correction (left), with metal artifact correction after normalized sinogram interpolation—in other words an NMAR method—(center) and with an embodiment of an inventive metal artifact correction (right) is shown, wherein at the top the general recordings and at the bottom a detailed representation extracted therefrom is illustrated enlarged in the region surrounding the metal implant.

FIG. 4 shows a patient with a bilateral hip prosthesis. In particular inside the prosthesis no further information is present after the NMAR method, as also is the case with other metal artifact correction methods of this type, but instead the region has a uniform gray-scale value. An embodiment of the inventive FSMAR method here provides a significantly better result, as can be recognized in particular in the enlarged illustration.

FIG. 5 shows an example with a coiling of an aneurism. After inserting the coil it is necessary to examine, with the aid of a CT image, whether bleeding is present in the tissue and whether the vessels in question are being supplied with blood. Here the area directly surrounding the coil is of interest. In the uncorrected image artifacts overlay this almost completely, so that it is barely possible to make an assessment. The corrected images make an assessment possible, wherein the right-hand pair of images with an embodiment of the inventive metal artifact correction produces particularly good results.

Finally FIG. 6 shows the CT representations of a so-called "internal fixation" for fixing the spinal column. In the layer illustrated in the region of the thorax, there are two screws in a vertebral body. In the uncorrected illustration on the left the screws are difficult to identify, whereas the NMAR method removes the dark and light artifacts, though large parts of the vertebral body are still blurred in proximity to the screws. An embodiment of the inventive FSMAR method corrects these artifacts further and conserves the vertebral body while retaining an optimum abundance of detail in the image regions not influenced by the metal.

Overall a method for reducing metal artifacts in CT image datasets is thus proposed with an embodiment of the invention, wherein by reconstructing a first CT image dataset with and a second CT image dataset without metal artifact correction, a weighted summation of a high-pass-filtered first and of a high-pass-filtered second CT image dataset with weightings which are dependent on the proximity to metal in the CT image datasets, and of a low-pass-filtered second CT image dataset, a significant image improvement is achieved.

Although the invention has been illustrated and described further in detail by the preferred exemplary embodiment, the invention is not restricted by the disclosed examples and other variations can be derived herefrom by the person skilled in the art, without departing from the scope of protection of the invention.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

LIST OF REFERENCE CHARACTERS

AF adaptive filtering
C1 CT system
C2 first emitter
C3 first detector
C4 second emitter
C5 second detector
C6 gantry housing
C8 patient couch
C9 system axis
C10 control and processing system
FSMAR results image
G weighting mask for metal
HP high-pass filter
HPF high-pass filtering
MAR_high high-pass-filtered metal-artifact-corrected CT image dataset
MAR_low low-pass-filtered metal-artifact-corrected CT image dataset
MET generation of a weighting mask G for metal that is present
P patient
$Prg_1$-$Prg_n$ computer programs
RECON reconstruction
RECON+MET_CORR reconstruction with metal correction
RD raw detector data
SCAN CT scan
TP low-pass filter
TPF low-pass filtering
U uncorrected first CT image dataset
U_af adaptively filtered CT image dataset
U_high high-pass-filtered first image dataset

What is claimed is:

1. A method for reducing metal artifacts in CT image datasets, comprising:
reconstructing a first CT image dataset without metal artifact correction;
reconstructing a second CT image dataset with metal artifact correction;
high-pass filtering the reconstructed first CT image dataset;
high-pass-filtering the reconstructed second CT image dataset;
low-pass-filtering the second CT image dataset; and
weight summing the high-pass filtered reconstructed first CT image dataset and the low-pass and high-pass-filtered second CT image dataset, the weightings being dependent on proximity to metal in the first and second CT image datasets.

2. A method for reducing metal artifacts in CT image data, comprising
using detector data from a scan of an object with incorporated metal;
reconstructing a first CT image dataset which dispenses with a metal artifact correction;
filtering the first CT image dataset with a high-pass filter to generate a high-pass-filtered first CT image dataset;
extracting a CT image dataset which exclusively shows metal from one of the reconstructed first CT image dataset and high-pass-filtered first CT image dataset, generating a metal-weighting function or metal-weighting mask wherein image regions with metal are relatively heavily weighted and image regions without metal are relatively slightly weighted and generating a metal-weighted high-pass-filtered first CT image dataset from the generated metal-weighting function or metal-weighting mask;
reconstructing a second CT image dataset using metal artifact correction;
filtering the second CT image dataset with the high-pass filter to generate a high-pass-filtered second CT image dataset;
filtering the second CT image dataset with a low-pass filter, complementary to the high-pass filter, to generate a low-pass-filtered second CT image dataset;
summing the low-pass-filtered second CT image dataset, the metal-weighted high-pass-filtered first CT image dataset and a complementarily metal-weighted high-pass-filtered second CT image dataset; and
at least one of storing and outputting an image resulting from the summing.

3. The method of claim 2, wherein the detector data is adaptively filtered with a noise filter before the reconstruction of at least one of the first and second CT image datasets in respect of a noise or a signal-to-noise ratio that is present, wherein a high noise or low signal-to-noise ratio requires strong filtering and vice versa.

4. The method of claim 2, wherein the first CT image dataset is adaptively filtered with a noise filter before the high-pass filtering in respect of a noise or a signal-to-noise ratio that is present, wherein a high noise or low signal-to-noise ratio requires strong filtering and vice versa.

5. The method of claim 2, wherein, in the second CT image dataset, the metal artifact correction is generated by a normalized sinogram interpolation.

6. The method of claim 2, wherein the metal-weighting function or metal-weighting mask is determined such that in image regions containing metal or their immediate vicinity a weighting of 1 is present and the weighting diminishes continuously to 0 as the distance from the metal increases.

7. A computing unit, comprising:
a non-transitory program memory configured to store program code; and
a processor configured to execute the program codes, the program code being configured to execute, when run on the processor, the method of claim 1 during operation.

8. A CT system comprising the computing unit of claim 7.

9. A C-arm system comprising the computing unit of claim 7.

10. The method of claim 1, the first CT image dataset is adaptively filtered with a noise filter before the high-pass filtering in respect of a noise or a signal-to-noise ratio that is present, wherein a high noise or low signal-to-noise ratio requires strong filtering and vice versa.

11. The method of claim 1, wherein, in the second CT image dataset, the metal artifact correction is generated by a normalized sinogram interpolation.

12. A computing unit, comprising:
a non-transitory program memory configured to store program code; and
a processor configured to execute the program codes, the program code being configured to execute, when run on the processor, the method of claim 2 during operation.

13. A CT system comprising the computing unit of claim 12.

14. A C-arm system comprising the computing unit of claim 12.

15. A non-transitory computer readable medium including program segments for, when executed on a computer device, causing the computer device to implement the method of claim 1.

16. A non-transitory computer readable medium including program segments for, when executed on a computer device, causing the computer device to implement the method of claim 2.

17. The method of claim 1, wherein the first and second CT image dataset are reconstructed from a single set of raw data.

18. The method of claim 2, wherein the first and second CT image dataset are reconstructed from a single set of raw data.

* * * * *